US008543413B2

(12) United States Patent
Muehlmeier et al.

(10) Patent No.: US 8,543,413 B2
(45) Date of Patent: Sep. 24, 2013

(54) TO-DO LISTS IN COMPUTERIZED HEALTHCARE ENVIRONMENT

(75) Inventors: Bryan Muehlmeier, Overland Park, KS (US); Stephanie St. Amand, Kansas City, MO (US); Kevin Winkel, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 1232 days.

(21) Appl. No.: 11/740,688

(22) Filed: Apr. 26, 2007

(65) Prior Publication Data

US 2007/0255594 A1 Nov. 1, 2007

Related U.S. Application Data

(60) Provisional application No. 60/745,960, filed on Apr. 28, 2006.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ......................................... 705/2–3
See application file for complete search history.

(56) References Cited

U.S. PATENT DOCUMENTS

| | | | |
|---|---|---|---|
| 4,662,537 A | 5/1987 | Wolf et al. | |
| 5,072,383 A * | 12/1991 | Brimm et al. | 705/2 |
| 6,434,531 B1 * | 8/2002 | Lancelot et al. | 705/3 |
| 7,469,219 B2 | 12/2008 | Goldberg | |
| 7,693,727 B2 * | 4/2010 | Moore | 705/2 |
| 2002/0165733 A1 | 11/2002 | Pulkkinen et al. | |
| 2004/0078231 A1 | 4/2004 | Wilkes et al. | |
| 2005/0033603 A1 * | 2/2005 | Suzuki et al. | 705/2 |
| 2005/0055242 A1 | 3/2005 | Bello et al. | |

OTHER PUBLICATIONS

Final Office Action for U.S. Appl. No. 11/740,626 dated Jan. 20, 2010.
Final Office Action for U.S. Appl. No. 11/740,626 dated Dec. 8, 2010.
Office Action for U.S. Appl. No. 11/740,626 dated Jun. 23, 2010.
Office Action for U.S. Appl. No. 11/740,626 dated Jul. 20, 2009.

* cited by examiner

*Primary Examiner* — Joseph Burgess
(74) *Attorney, Agent, or Firm* — Shook, Hardy & Bacon L.L.P.

(57) ABSTRACT

Electronic to-do lists are provided in a computerized healthcare environment for managing and documenting events during clinical care processes. A to-do list includes events that may need to be completed and, in some cases, documented during a clinical care process. The to-do list may be generated in response to a selection of a to-do macro including data associated with a number of clinical events that need to be completed during the clinical care process. As events are completed by clinicians during the process, the to-do list may be used to document the completion of the event. As such, clinicians may readily identify events that have been performed, as well as events that have yet to be performed. In some cases, a clinical event in a to-do list may include associated details, which may be used to populate information in an electronic record when the clinical event is indicated as completed.

14 Claims, 14 Drawing Sheets

| ☐ MACROS | | | | | | _ ▢ ✕ |
|---|---|---|---|---|---|---|
| | | ANESTHESIA -GENERAL- | | | | |
| EXECUTE | TO DO | EVENT | TYPE | DETAILS | DATE | TIME | EDIT |
|---|---|---|---|---|---|---|---|
| | ✓ | URINE VOIDED | ACTIONS | | 4/26/2006 | 15:51 | ✎ |
| | ✓ | ANESTHESIA INDUCTION TIME | ACTIONS | | 4/26/2006 | 15:51 | ✎ |
| | ✓ | LABS | ACTIONS | | 4/26/2006 | 15:51 | ✎ |
| | ✓ | WARMING DEVICES USED | ACTIONS | | 4/26/2006 | 15:51 | ✎ |
| | ✓ | ANESTHESIA STOP | ACTIONS | | 4/26/2006 | 15:51 | ✎ |
| ✓ | | PATIENT PREP | ACTIONS | | 4/26/2006 | 15:51 | ✎ |

MAINTAIN MACRO...        EXECUTE   CANCEL

FIG. 3.

Figures 6A, 6B:
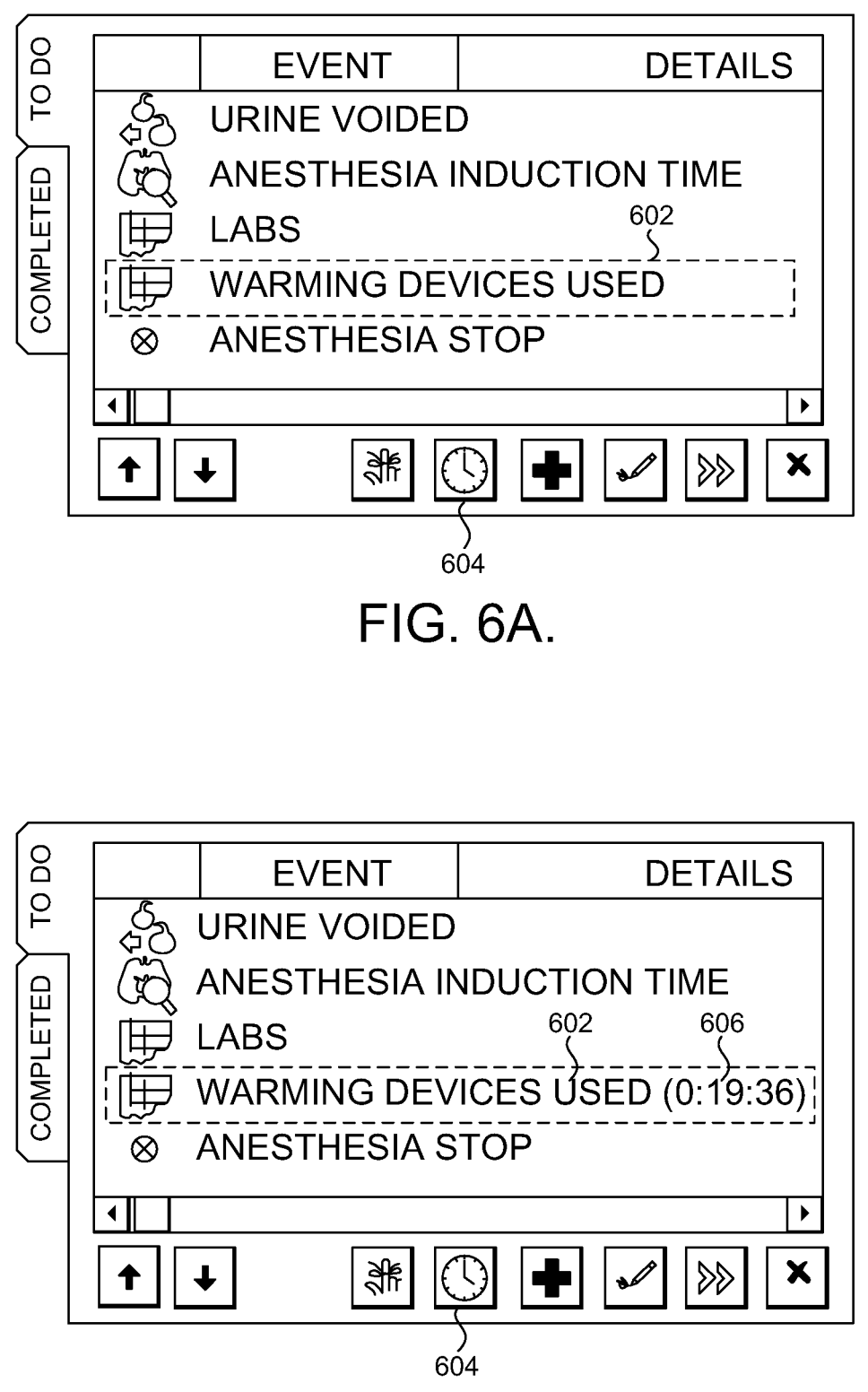

| | EVENT | DETAILS |
|---|---|---|
| | URINE VOIDED | |
| | ANESTHESIA INDUCTION TIME | |
| | LABS | 602 |
| | WARMING DEVICES USED | |
| | ANESTHESIA STOP | |

| | EVENT | DETAILS |
|---|---|---|
| | URINE VOIDED | |
| | ANESTHESIA INDUCTION TIME | |
| | LABS | 602   606 |
| | WARMING DEVICES USED (0:19:36) | |
| | ANESTHESIA STOP | |

TO-DO LISTS IN COMPUTERIZED HEALTHCARE ENVIRONMENT

CROSS-REFERENCE TO RELATED APPLICATIONS

This application claims the benefit of U.S. Provisional Application No. 60/745,960 filed Apr. 28, 2006. Additionally, this application is related by subject matter to the invention disclosed in U.S. application Ser. No. 11/740,626, filed on even date herewith, entitled "TO-DO LISTS WITH TIMER FUNCTIONALITY IN COMPUTERIZED HEALTHCARE ENVIRONMENT," which is assigned or under obligation of assignment to the same entity as this application, and incorporated in this application by reference.

STATEMENT REGARDING FEDERALLY SPONSORED RESEARCH OR DEVELOPMENT

Not applicable.

BACKGROUND

To ensure patient safety and quality of care in healthcare settings, it is often important for healthcare facilities to comply with a variety of standards and protocols. For example, healthcare facilities must often comply with a variety of mandatory standards for licensure and/or accreditation. Additionally, many healthcare facilities strive to comply with voluntary standards, such as those for accreditation by the Joint Commission of Accreditation of Healthcare Organizations. Further, many healthcare facilities set their own internal standards that meet or exceed these mandatory and voluntary external standards. These internal and external standards are typically driven by best practices and accordingly set forth procedures with which clinicians, such as physicians and nurses, must comply. Additionally, documentation of clinicians' practices is often required to ensure compliance.

For many clinical care processes, such as in the context of anesthesia and surgical settings, standards for patient safety and quality of care are important, for instance, to reduce the chance and severity of complications. For example, standards often dictate events to be completed during an operation, as well as any required documentation of those events. Depending on the length and complexity of an operation, this may include a long list of events. Accordingly, it may be difficult for clinicians to remember each event that must be completed and documented during operations. Additionally, some operations may be extremely long, making it difficult for clinicians to remember events that occurred earlier in the operation. Some operations may be complex and involve a multitude of clinicians, further making it difficult for clinicians to remember which events have been completed and which events have yet to be completed.

Currently, some clinicians may work from memory of events that need to be performed during a clinical care process. However, such practice may be prone to error depending on the complexity of the process. In some cases, clinicians may work from a list of events to be completed during the clinical care process. However, such lists are not actionable and do not provide a convenient approach to tracking event completion. Additionally, when an event requires documentation, the clinician must manually document the event and any necessary details either during the clinical care process, which is burdensome, or after the clinical care process is completed, which is susceptible to memory error. There is currently no convenient approach to tracking and documenting event completion. Additionally, there is currently no convenient approach to timing events or providing reminders for events during a clinical care process. Further, there is currently no convenient approach to coordinating events among multiple clinicians participating in the same clinical care process.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to providing electronic to-do lists in computerized healthcare environments. A to-do list in accordance with an embodiment of the present invention provides, among other things, an indication of events that need to be completed during a clinical care process. As clinicians perform events during the process, the to-do list may be used to document the completion of each event. As such, the to-do list provides a quick and convenient way for clinicians to readily identify which events have been completed, as well as which events have not yet been completed. Additionally, the to-do list provides a quick and convenient way for clinicians to document events for compliance purposes and the like.

Further embodiments of the present invention are directed to incorporating timer functionality with to-do lists. In accordance with such embodiments, users may set elapsed and/or countdown timers for events on a to-do list. Additionally, users may set alerts and reminders for events on the to-do list based on the timer functionality. In some embodiments, timer and alert/reminder functionality may be automatically provided for associated events.

In yet further embodiments of the present invention, events may be shared among two or more to-do lists. The execution of a shared event may be coordinated among the to-do lists that include the shared event.

Accordingly, in one aspect, an embodiment of the present invention is directed to a method in a clinical computing environment for providing an electronic to-do list for tracking completion of a plurality of clinical events during a clinical care process. The method includes receiving a user selection of a to-do macro for a type of clinical care process, the to-do macro including data associated with a number of clinical events to be completed for the type of clinical care process. The method also includes generating a to-do list based on the selected to-do macro, the to-do list providing an indication for at least a portion of the clinical events. The method further includes presenting the to-do list to a user via a user interface and receiving user input indicative of completion of one or more selected clinical events. The method still further includes providing an indication that the selected clinical events have been completed based on the user input.

In another aspect of the invention, an embodiment is directed to a method for documenting a clinical event performed during a clinical care process. The method includes presenting an electronic to-do list, the to-do list including an indication of a plurality of clinical events to be performed during a clinical care process, wherein at least one clinical event is associated with details regarding the clinical event. The method also includes receiving user input indicating that the clinical event has been completed. The method further includes documenting the completion of the clinical event in an electronic record based on the user input, wherein the details associated with the clinical event are used to populate information in the electronic record.

In yet another aspect, an embodiment of the invention is directed to a method in a clinical computing environment for providing an electronic to-do list for tracking completion of a number of clinical events during a clinical care process and documenting the completion of at least one of the clinical events in an electronic record. The method includes receiving a user selection of a to-do macro for a type of clinical care process, the to-do macro comprising data associated with a number of clinical events to be completed for the type of clinical care process, wherein at least one clinical event is associated with details regarding the clinical event. The method also includes generating a to-do list based on the selected to-do macro, the to-do list providing an indication for at least a portion of the clinical events. The method further includes presenting the to-do list to a user via a user interface and receiving user input indicative of completion of the clinical event that have details associated therewith. The method still further includes providing an indication that the clinical event has been completed and documenting the completion of the clinical event in an electronic record based on the user input, wherein the details associated with the clinical event are used to populate information in the electronic record.

BRIEF DESCRIPTION OF THE SEVERAL VIEWS OF THE DRAWINGS

The present invention is described in detail below with reference to the attached drawing figures, wherein:

FIG. 3 is an illustrative screen display showing an exemplary macro dialog box in accordance with an embodiment of the present invention;

FIGS. 6A and 6B are illustrative screen displays showing elapsed timer functionality in a to-do list in accordance with an embodiment of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems for providing electronic to-do lists in computerized healthcare environments. Embodiments of the present invention further provide computerized methods and systems for providing to-do lists with timer functionality. Still further, embodiments of the present invention provide computerized methods and systems for sharing events across to-do lists. Having briefly described an overview of embodiments of the present invention, an exemplary operating environment is described below.

Figure 1:
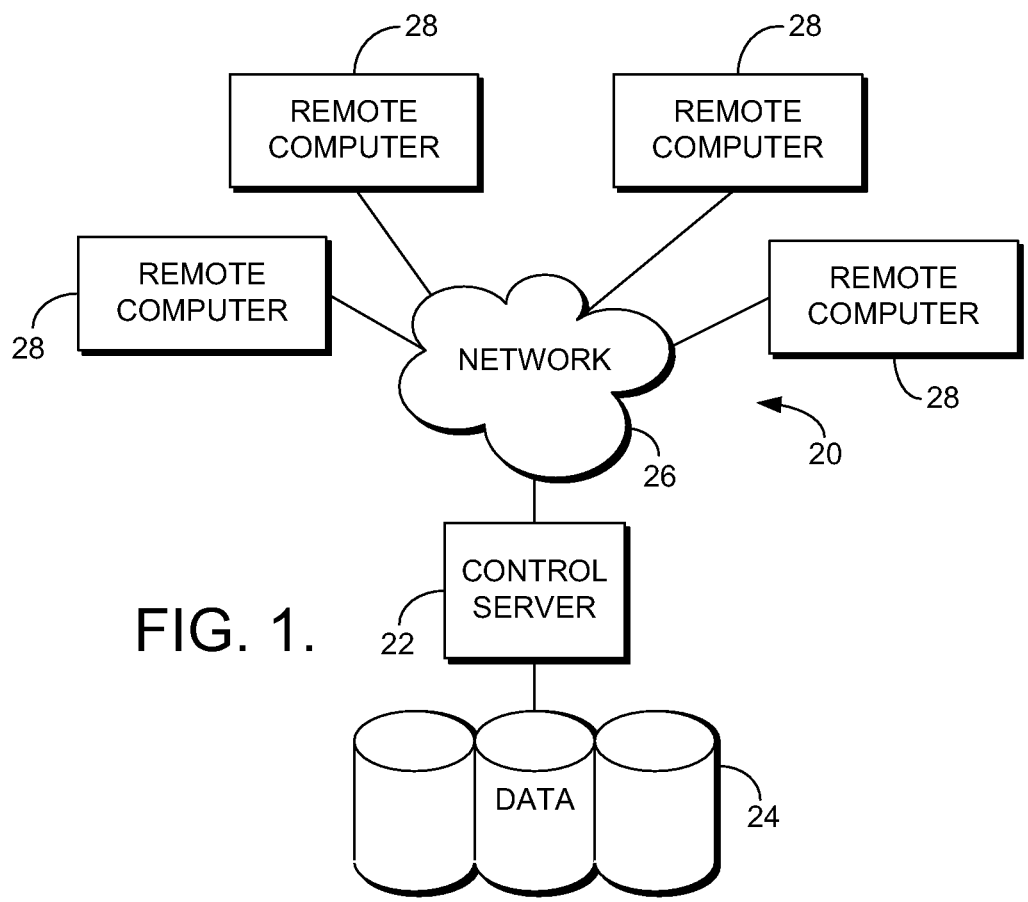
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

As discussed previously, clinical care processes, such as surgical procedures, for instance, may often be long and complex, making it difficult for clinicians to remember events that need to be completed, as well as events that have already been completed. For example, it may be difficult for a clinician to remember an event that occurred during the third hour of a twelve hour operation. In some cases, the difficulty to remember events may be further compounded by the complexity of the case and the number of clinicians involved. Additionally, many of the events performed during a clinical care process need to be documented. Embodiments of the present invention are directed to providing electronic to-do lists within a computerized healthcare environment. A to-do list in accordance with embodiments of the present invention provides a quick and convenient way for a clinician to access and view events that need to be completed and/or documented for a clinical care process. Additionally, the to-do list provides a quick and convenient way for the clinician to document the completion of events as they are performed. As such, using the to-do list, a clinician may easily identify events that have been completed, as well as those events that have yet to be performed. Moreover, the to-do list allows the clinician to collect accurate documentation of events during a clinical care process for compliance purposes and the like.

To-do lists may be driven and defined by workflows comprising various events that may need to be completed and, for some events, documented during clinical care processes. For example, best practices and standards may be used by a healthcare facility to define pre-built standards of care for various clinical care processes. Each pre-built standard of care comprises a series of events that may need to be performed to ensure patient quality of care. Using the pre-built standard of care for a particular clinical care process, a "macro" may be generated. When a macro associated with a particular clinical care process is selected by a user, the macro generates a to-do list for the clinical care process and presents the to-do list to the user. The to-do list indicates those events that need to be completed during the clinical care process. Additionally, zero, one, or many of the events included in the to-do list may be events that need to be documented during the clinical care process. In some cases, separate to-do lists may be beneficial for a single clinical care process. For example, it may be desirable to have a separate to-do list for each clinician involved in the clinical care process. Accordingly, multiple macros may be defined for a particular clinical care process or a single macro, when executed, may generate multiple to-do lists.

Additionally, to-do lists may be populated using electronic "preference cards." Surgeons often have individualized preferences that differ from surgeon to surgeon and from procedure to procedure. Traditionally, such preferences are captured manually using "preference cards" that may be pulled by a nurse, for example, before beginning a particular procedure. These preferences could be captured by the system in electronic "preference cards," which when selected could generate a to-do list or otherwise further populate an existing to-do list (e.g., add or reorder events in a to-do list generated by a macro).

Figure 2:
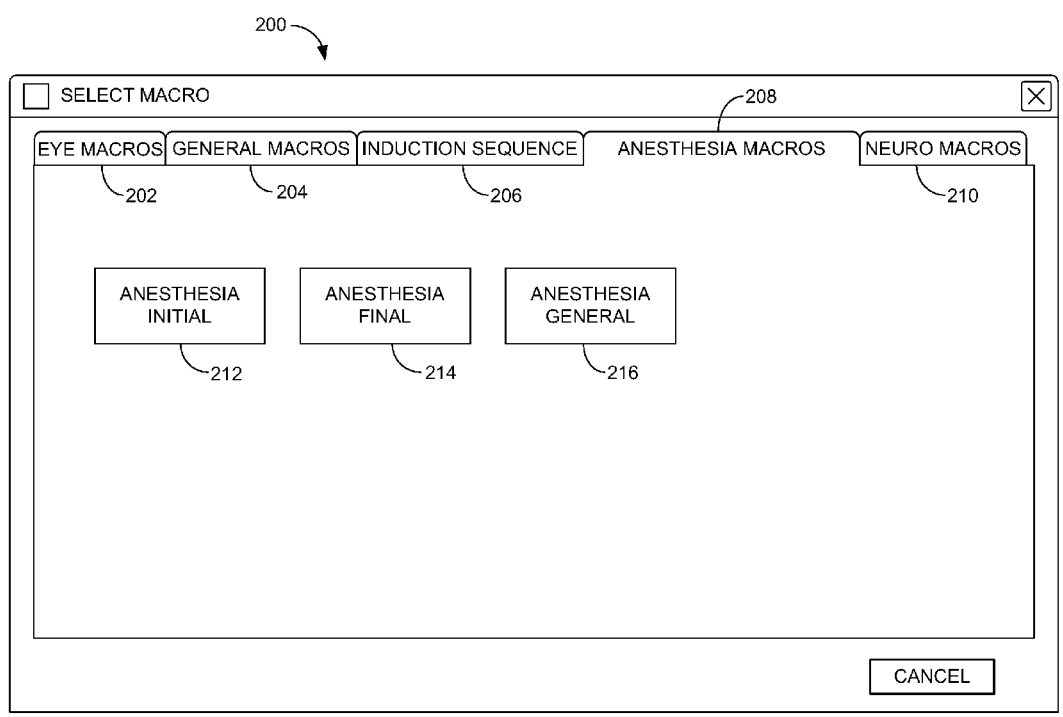
FIG. 2 is an illustrative screen display showing an exemplary macro selection dialog box in accordance with an embodiment of the present invention.

Referring to FIGS. 2 and 3, screen displays are provided illustrating the selection and execution of a macro to generate a to-do list in accordance with an embodiment of the invention. Referring initially to FIG. 2, a macro selection dialog box 200 is illustrated. The macro selection dialog box 200 allows a user to browse available macros and select a particular macro for execution. As shown in FIG. 2, the macro selection dialog box 200 generally includes a number of tabs 202, 204, 206, 208, 210, each tab including macros related to a particular clinical context. For instance, in FIG. 2, the user has selected the "Anesthesia Macros" tab 208 to view anesthesia related macros. The "Anesthesia Macros" tab 208 includes three user-selectable buttons, each button allowing for the selection of a particular macro and including: "Anesthesia—Initial" 212, "Anesthesia—Final" 214, and "Anesthesia—General" 216.

When a user selects a macro, such as by selecting the "Anesthesia—General" button 216, for instance, details of the selected macro may be viewed via a macro dialog box, such as the macro dialog box 300 illustrated in FIG. 3. The macro dialog box 300 indicates the events 302 included in the macro, as well as additional information associated with each event. For instance, each event may have associated details 304. The details for a particular event may include information such as comments regarding how the event should be performed. If desired, a user may edit an event and its associated information by selecting an edit button 306 for the event. A user may also specify, via an execute selection box 308 and a to-do selection box 310, whether each event should be included in a to-do list or automatically executed when the macro is executed. For instance, a user may wish to execute a macro after performing one or more events and, as such, have those events automatically indicated as performed and/or documented upon execution of the macro. In the present example shown in FIG. 3, the user has already prepped the patient and has selected the execute selection box 312 for the patient prep event 314. Accordingly, when the user executes the macro by selecting the execute button 316, a to-do list is generated including those events having a corresponding to-do selection box selected. The patient prep event, however, is automatically executed upon execution of the macro such that the event is shown as completed and/or documented as completed.

Figure 4A:
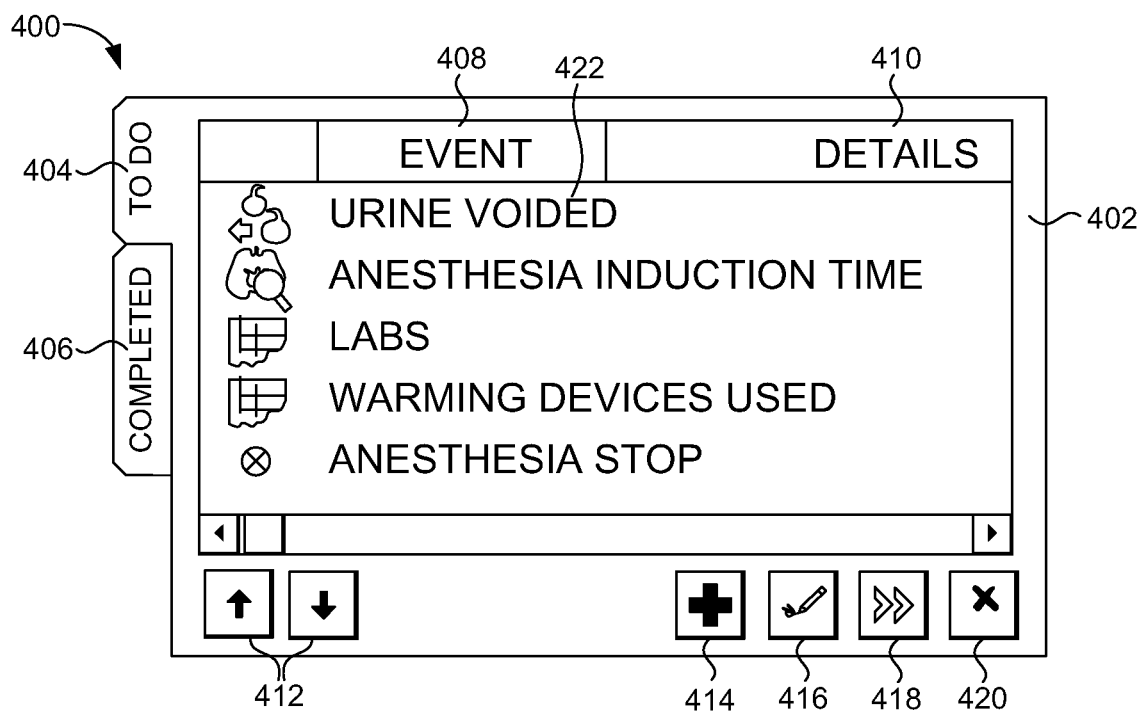
FIGS. 4A-4C are illustrative screen displays showing an exemplary to-do list and execution of an event in the to-do list in accordance with an embodiment of the present invention.

Referring now to FIG. 4A, a screen display showing an exemplary to-do list 400 in accordance with an embodiment of the present invention is illustrated. The to-do list 400 shown in FIG. 4A may have been generated, for instance, when a user executes the macro from the macro dialog box 300 of FIG. 3. In some cases, however, a user may manually create a to-do list (e.g., in the event that a macro and/or preference card has not been prepared or is otherwise unavailable for a particular procedure).

As shown in FIG. 4A, the to-do list 400 is presented in a dialog box 402, which includes a "To-Do" tab 404 and a "Completed" tab 406. The "To-Do" tab 404 is currently selected and shown in FIG. 4A and generally includes a list of events 408 to be completed and, if appropriate, documented during the clinical care process. Additional information, such as details 410, may be also presented for each event in the dialog box 402.

The to-do list 400 includes a number of selectable control buttons, including sequence buttons 412, a new event button 414, an edit button 416, an execute button 418, and a remove button 420. By using the control buttons, a user may interact with the to-do list 400. For example, by selecting the new event button 414, a user may add an event to the to-do list 400. In various embodiments of the present invention, a user may add a new event by creating a free-text event and/or by selecting an event from a list of predefined events. A user may edit an existing event and corresponding information (including details of the event) by selecting the event and clicking the edit button 416. In some cases, a user may reorder the events provided in the to-do list 400 using the sequence buttons 412. For instance, a user may select a particular event, such as the "Urine Voided" event 422, and select one of the sequence buttons to move the event up or down in the list of events. In other cases, a user may reorder the events by simply clicking on an event and dragging the event to a different location in the list. A user may also remove a particular event from the to-do list 400, for example, by selecting the event and clicking the remove button 420.

Figure 4B:
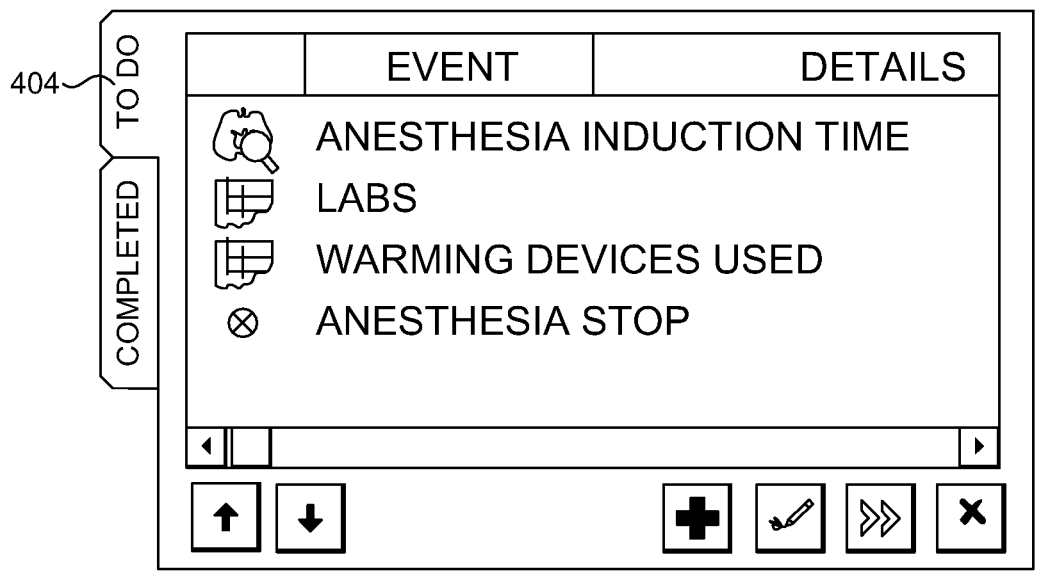
Figure 4C:
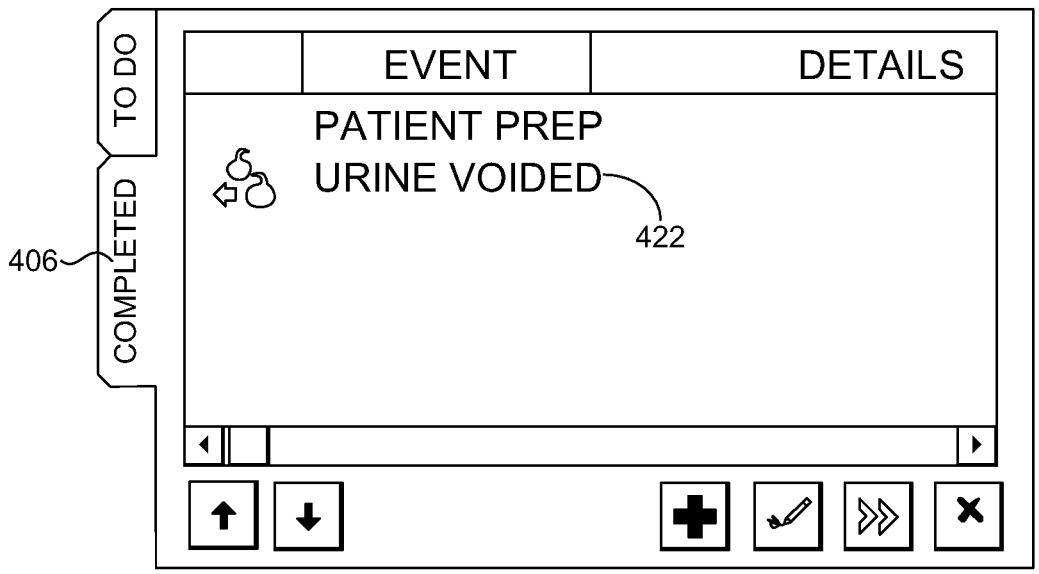

As an event is carried out during a clinical care process, a user may use the to-do list 400 to show the event as completed, and if appropriate for the event, document the completion of the event. The user may do so by selecting the event and clicking the execute button 418. When an event has been executed, the event is moved from the "To-Do" tab 404 to the "Completed" tab 406. For example, when the "Urine Voided" event 422 in FIG. 4A has been completed, the user selects the event 422 and the execute button 418. As shown in FIG. 4B, the "Urine Voided" event has been removed from the "To-Do" tab 404 as a result of the action. Additionally, as shown in FIG. 4C, the event is now shown on the "Completed" tab 406.

As mentioned previously, the completion of some events during a clinical care process may also need to be documented in a record, such as, for example, a preoperative record, a perioperative record, or a flowsheet for the procedure. When an event that requires documentation is executed at a to-do list, the completion of the event may be automatically documented in an appropriate electronic record. In some cases, documentation required for an event includes not only information indicating that the event was performed but also details regarding how the event was performed. To-do lists in accordance with embodiments of the invention provide a convenient approach to documenting such information. In particular, as discussed previously, each event in a to-do list may be automatically pre-populated with details regarding how an event should be performed. These details may be used to automatically populate the required documentation. If a clinician deviates from the pre-populated details included in a to-do list, the clinician may simply edit the details in the to-do list, and the edited details are then used for documentation purposes when the event is executed.

Figure 5:
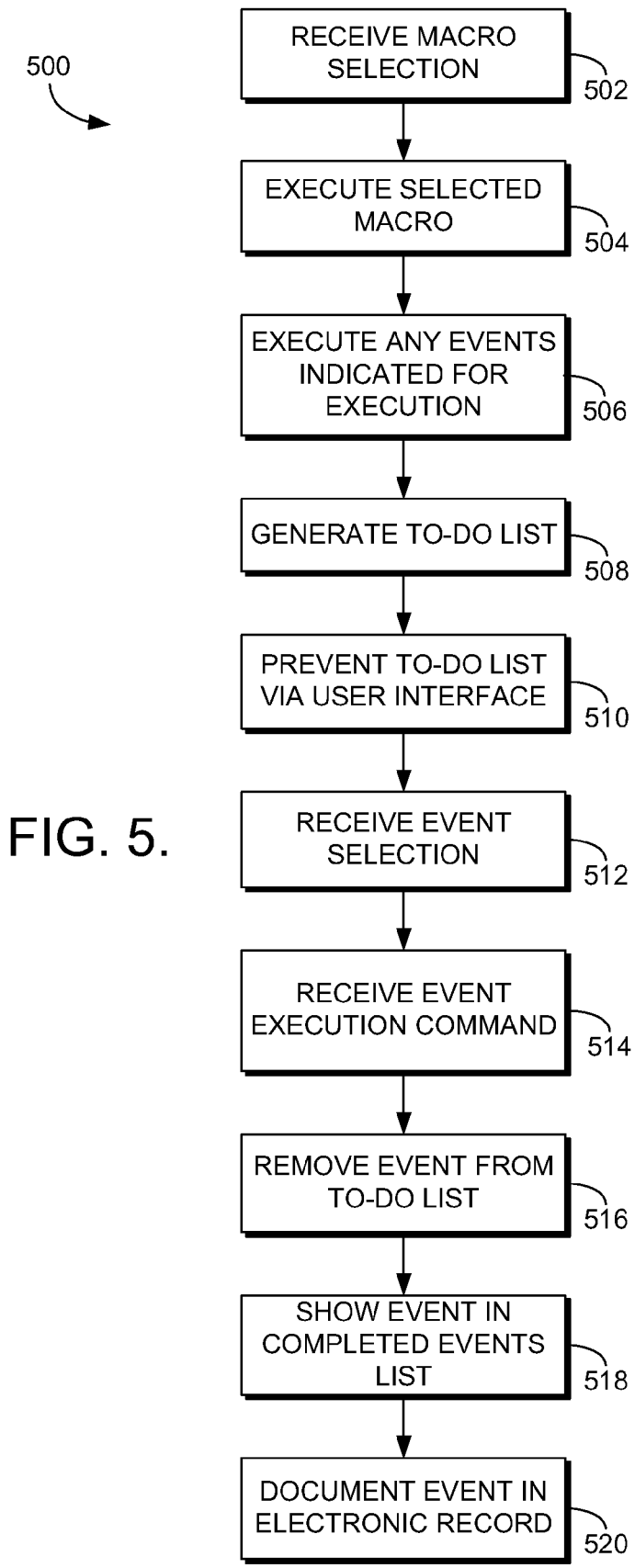
FIG. 5 is a flow diagram showing a method for generating a to-do list from a macro and using the to-do list to track event completion in accordance with an embodiment of the present invention.

Turning to FIG. 5, a flow diagram is provided illustrating a method 500 for generating a to-do list from a macro and using the to-do list to execute an event in accordance with an embodiment of the present invention. Initially, as shown at block 502, a macro selection is received. The selected macro is then executed at block 504. Any events indicated in the macro as events to be executed upon execution of the macro are automatically executed, as shown at block 506. Additionally, a to-do list is generated based on the remaining events included in the macro, as shown at block 508. The generated to-do list is presented to a user via a user interface at block 510. As a clinician completes an event, the clinician may select the event in the to-do list presented via the user interface, as represented at block 512. Additionally, the clinician may provide an execution command using the to-do list presented via the user interface, as shown at block 514. Accordingly, at block 516, the event is removed from the to-do list. Additionally, as shown at block 518, the event may be added to (and shown in) a completed events list. Further, if the event is one that requires documentation, the event may be automatically documented in an appropriate electronic record, as shown at block 520. Any details associated with the event may also be used to populate the electronic record.

In some embodiments of the present invention, timer functionality may be provided around events on a to-do list. As will be illustrated in further detail below, a running timer showing elapsed time for an event may be started, stopped, restarted, and/or reset. Additionally, a countdown timer may be provided for an event that may be started, stopped, restarted, and/or reset. In some cases, alerts and/or reminders may be set based on the timer functionality. It should be noted that timer functionality may be provided individually for each event. This is advantageous as a user may wish to simultaneously but independently time multiple events on a to-do list.

In some embodiments, a to-do list may provide elapsed timer functionality such that when activated, an elapsed time indication may be presented for a selected event. The elapsed timer function provides a convenient mechanism for clinicians to time individual events on a to-do list. The functionality may be useful, for instance, in cases in which a clinician wishes to know how long it takes to complete a particular event. One such embodiment may be described in further detail by referring to FIG. 6A and FIG. 6B. Referring initially to FIG. 6A, when a clinician begins to warm devices or otherwise wishes to time the "Warming Devices Used" event 602, the user may select the "Warming Devices Used" event 602 and click on the timer button 604 to begin the elapsed timer. As shown in FIG. 6B, in response to the user actions, an elapsed time indication 606 is provided in association with the event 602. A user may subsequently stop (i.e., pause) and restart the timer by repeatedly selecting the event 602 and clicking on the timer button 604. Additionally, in some cases, the user may reset the timer for the event 604.

Figure 7:
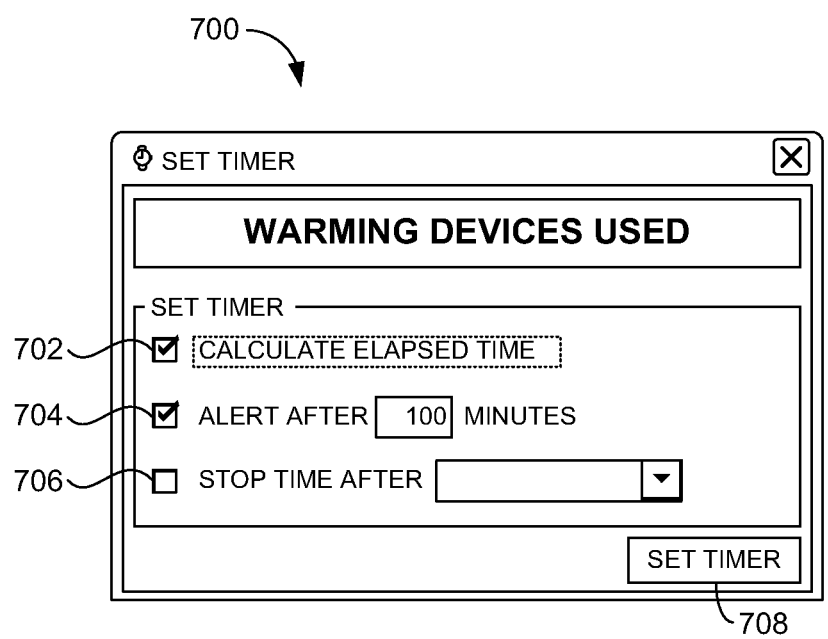
FIG. 7 is an illustrative screen display showing an elapsed timer dialog box in accordance with an embodiment of the present invention.

In another embodiment providing elapsed timer functionality, an elapsed timer dialog box may be presented when a user selects the timer button 604. For example, when a user selects the "Warming Devices Used" event 602 and clicks the timer button 604 in FIG. 6A, the elapsed timer dialog box 700 shown in FIG. 7 is presented. The dialog box 700 allows the user to set various parameters of an elapsed timer for the selected event. For example, the user may generally select to have an elapsed time indication presented by selecting the "Calculate Elapsed Time" option 702. Additionally, a user may select to have an alert 704 provided and may indicate a specified elapsed time at which the alert should be provided. Further, the user may set the timer to stop 706 after a particular event has occurred or a specified time period has elapsed. After setting the timer parameters for the event, the user may select the "Set Timer" button 708, thereby starting the elapsed timer for the selected event.

Figure 8:
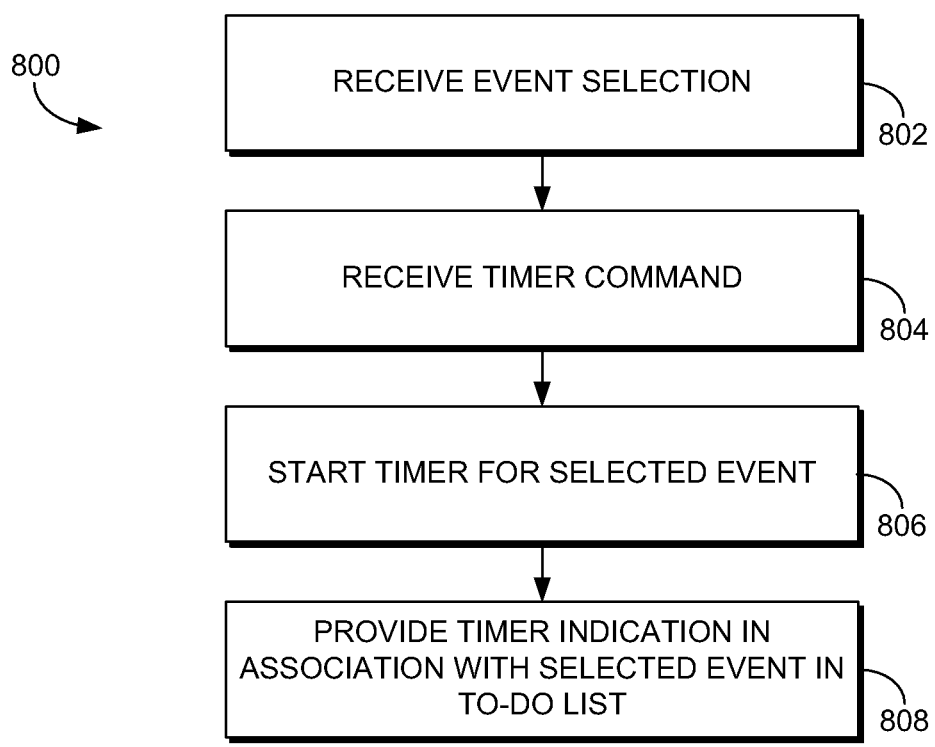
FIG. 8 is a flow diagram showing a method for timing an event in a to-do list in accordance with an embodiment of the present invention.

Turning to FIG. 8, a flow diagram is provided illustrating a method 800 for timing an event in a to-do list in accordance with an embodiment of the present invention. Initially, as shown at block 802, an event selection is received using a to-do list presented via a user interface. Additionally, a timer command is received via the to-do list, as shown at block 804. Based on the event selection and timer command, a timer is started for the selected event, as shown at block 806. A timer indication is also provided in the to-do list in association with the selected event, as shown at block 808. In some embodiments, the timer indication may be user-selectable as an elapsed timer or a countdown timer. The timer may subsequently be selectively started and stopped by a clinician using the to-do list presented via the user interface.

Figure 9A:
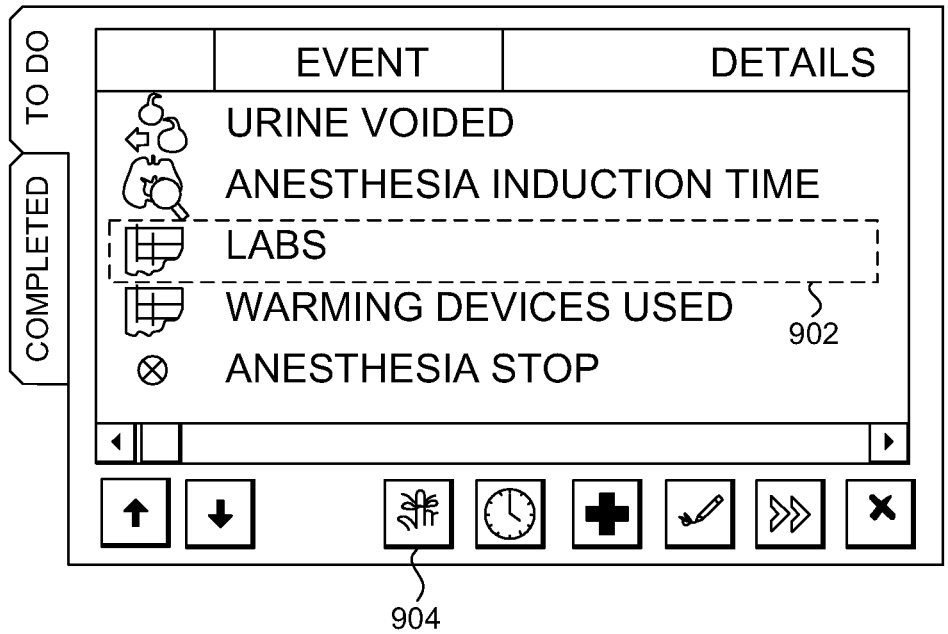
FIGS. 9A and 9B are illustrative screen displays showing reminder functionality in a to-do list in accordance with an embodiment of the present invention.
Figure 9B:
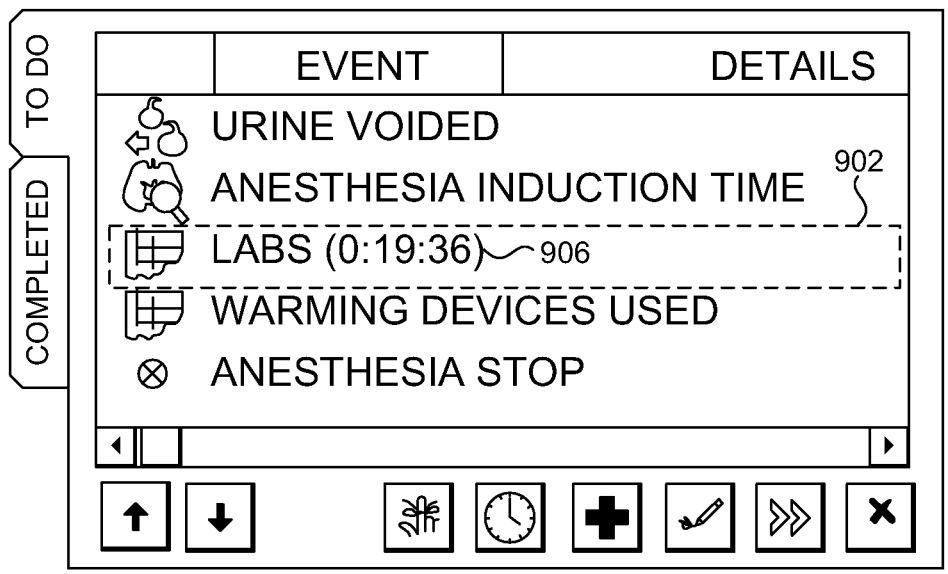
Figure 10:
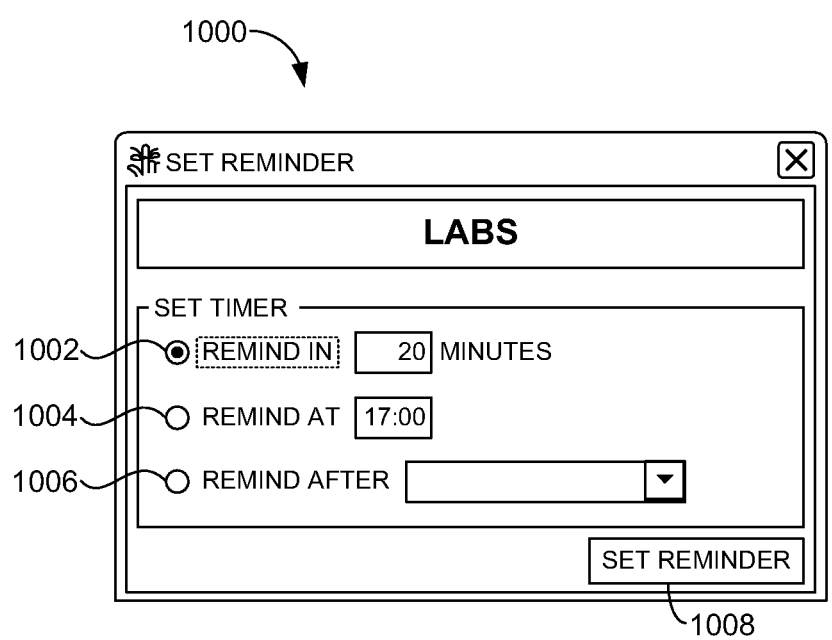
FIG. 10 is an illustrative screen display of a reminder dialog box in accordance with an embodiment of the present invention.

In further embodiments of the present invention, a user may set reminders for one or more selected events. For instance, events may need to be completed at particular points during the case. Accordingly, a user may set reminders for any such events such that the system provides an indication at a specified time. In various embodiments, the user may either set a specific time for a reminder (e.g., 9:30 a.m.) or may set a specified countdown duration (e.g., 30 minutes) after which a reminder is provided. For example, referring to FIG. 9A, a user may wish to have a reminder to draw specimens for laboratory testing. To set a reminder, the user may select the "Labs" event 902 and click on the reminder button 904. In response to the user selections, a dialog box, such as the reminder dialog box 1000 shown in FIG. 10, may be provided. The reminder dialog box 1000 allows the user to set a reminder to be provided: (1) after a selected duration 1002; (2) at a specific time 1004; or (3) after a selected event occurs 1006. In the example shown in FIG. 10, the user has specified a duration of 20 minutes. After configuring a reminder, the user may select the "Set Reminder" button 1008 to set the reminder. In some cases, a countdown timer may be presented in the to-do list with an event showing the time remaining until a set reminder. For example, referring to FIG. 9B, in response to setting the reminder for the "Labs" event 902, a time remaining indication 906 has been provided in association with the event 902.

Alerts and reminders may be provided in any of a variety of different ways within the scope of the present invention. For example, in some embodiments, an alert/reminder may comprise some visual indicia, such as showing the event as flashing, highlighting the event, showing the event in a different color, and/or presenting a dialog box with the alert/reminder.

Alternatively or additionally, an alert/reminder may comprise an audible indication to notify the user of the alert/reminder.

Figure 11:
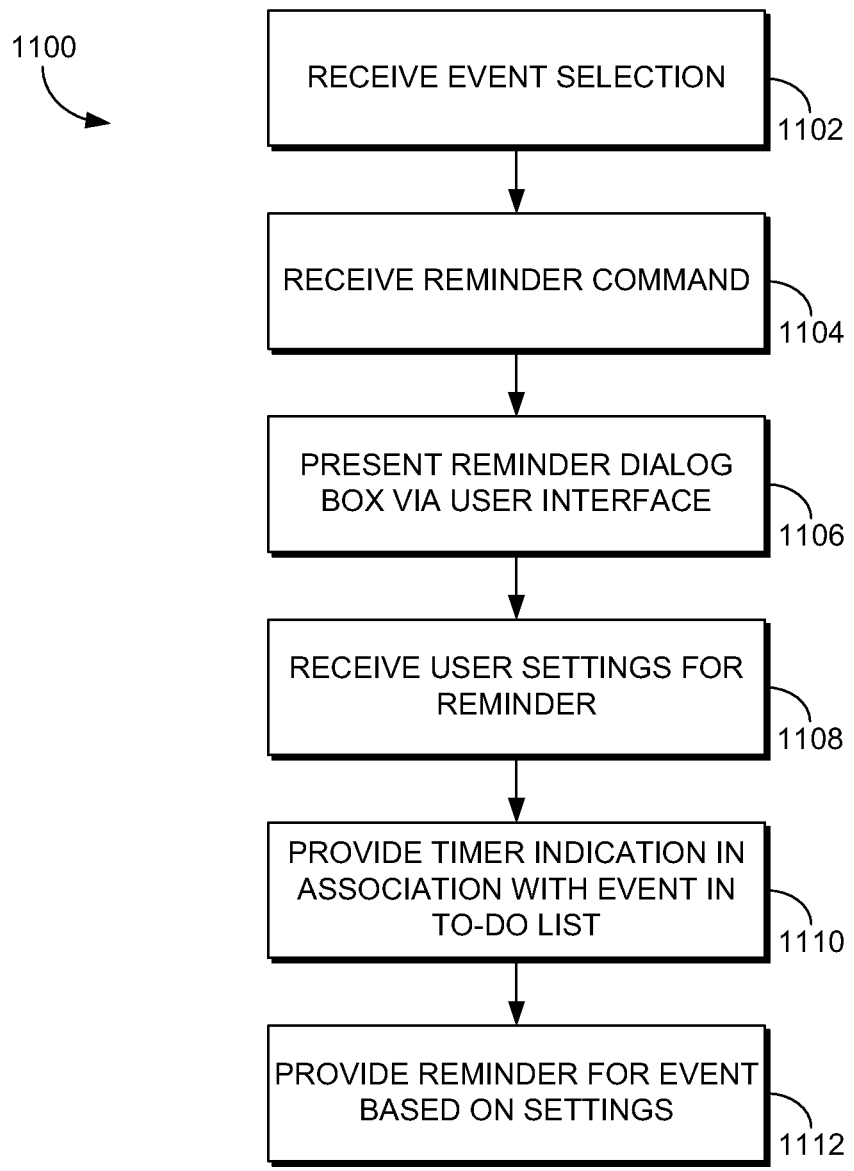
FIG. 11 is a flow diagram showing a method for providing a reminder for an event in a to-do list in accordance with an embodiment of the present invention.

Turning to FIG. 11, a flow diagram is provided illustrating a method 1100 for receiving user settings for a reminder for an event in a to-do list and providing a reminder based on the settings in accordance with an embodiment of the present invention. Initially, as shown at block 1102, an event selection is received. Additionally, a reminder command is received at block 1104. Based on the command, a reminder dialog box is presented via a user interface, as shown at block 1106. User settings for the reminder are received via the reminder dialog box, as shown at block 1108. The settings may include, for instance, when to provide the reminder for the event (e.g., specific time or countdown duration) and whether to provide any timer indication in association with the selected event based on the reminder. If selected, a timer indication is provided in association with the selected event in the to-do list, as shown at block 1110. A reminder is provided for the selected event based on the reminder settings, as shown at block 1112.

In some cases, two or more events may be associated, such as events that include both a start event and a stop event. In such cases, clinicians may wish to track the time between the associated events. For example, best practices may dictate that the time between associated events should meet a minimum duration or, alternatively, not exceed a maximum duration. In an embodiment, when an initial event (e.g., a start event) is executed, an elapsed time and/or countdown time may be provided automatically for a subsequent associated event (e.g., a stop event). By providing such a timer, a clinician may readily identify whether a minimum duration between events has been satisfied or when a maximum duration between events expires. In some embodiments, the minimum or maximum duration between events may be hard-coded in the to-do list. In other embodiments, a user may manually set the duration. In the case of a maximum duration, an alert may be provided if the subsequent event has not been executed when the duration expires (and/or a reminder may be provided at a set time before the duration expires). In the case of a minimum duration, an alert may be provided if a clinician attempts to execute the subsequent event before the minimum duration has run.

Figure 12A:
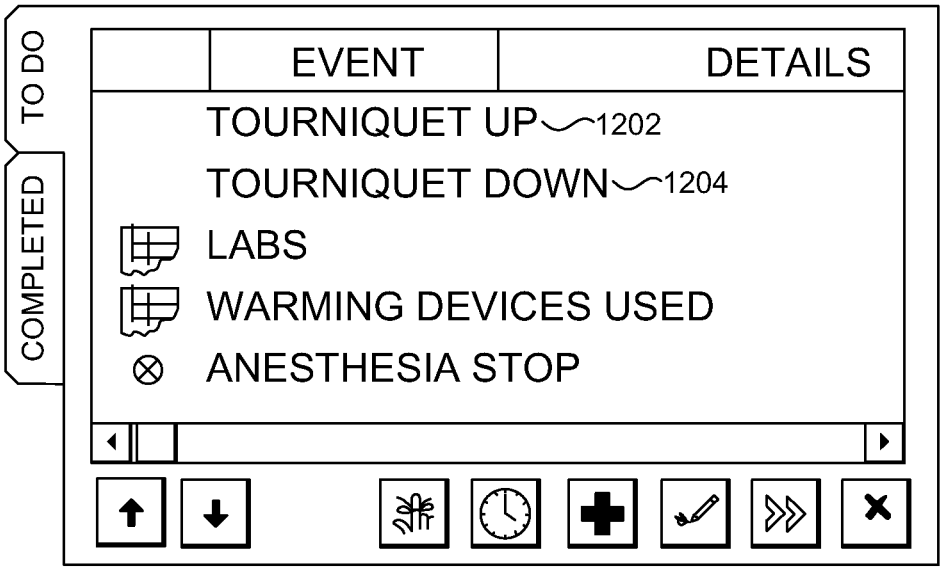
FIGS. 12A and 12B are illustrative screen displays showing timer functionality for associated events in accordance with an embodiment of the present invention.
Figure 12B:
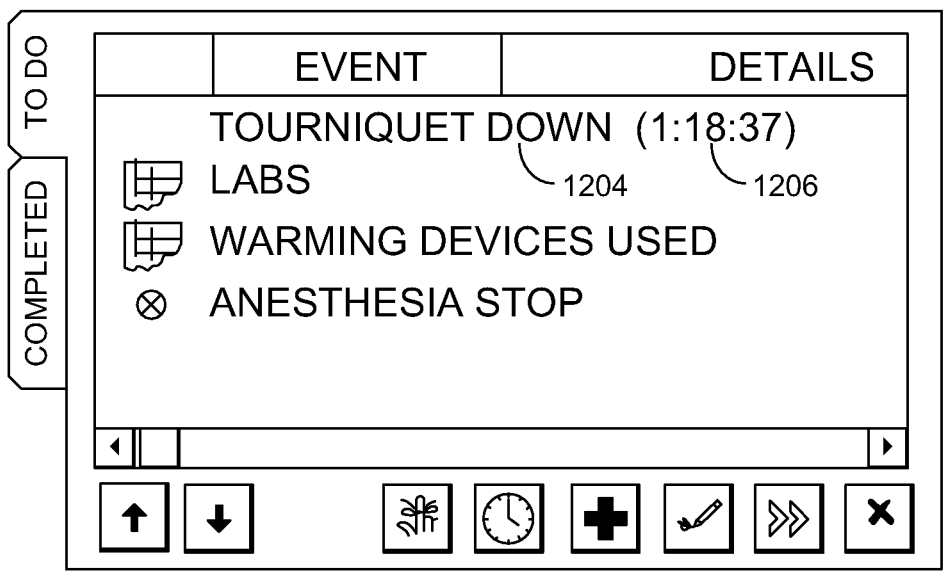

As an example of a maximum duration, referring to FIG. 12A, a to-do list is illustrated having a "Tourniquet Up" event 1202 and a corresponding "Tourniquet Down" event 1204. Best practices dictate that a tourniquet typically should not be up for more than 120 minutes. Accordingly, when the "Tourniquet Up" event 1202 is executed, a countdown time 1206 may be provided with the "Tourniquet Down" event 1204, as shown in FIG. 12B, indicating the time until the event should be completed. In some embodiments, an elapsed time may be provided in addition to or in lieu of the countdown time 1206. If the "Tourniquet Down" event 1204 has not been executed when the 120 minute duration expires, an alert may be provided. Additionally, a reminder may be provided before the duration expires. For example, in one embodiment, the countdown time 1206 may be configured to begin flashing when five minutes are remaining.

Figure 13:
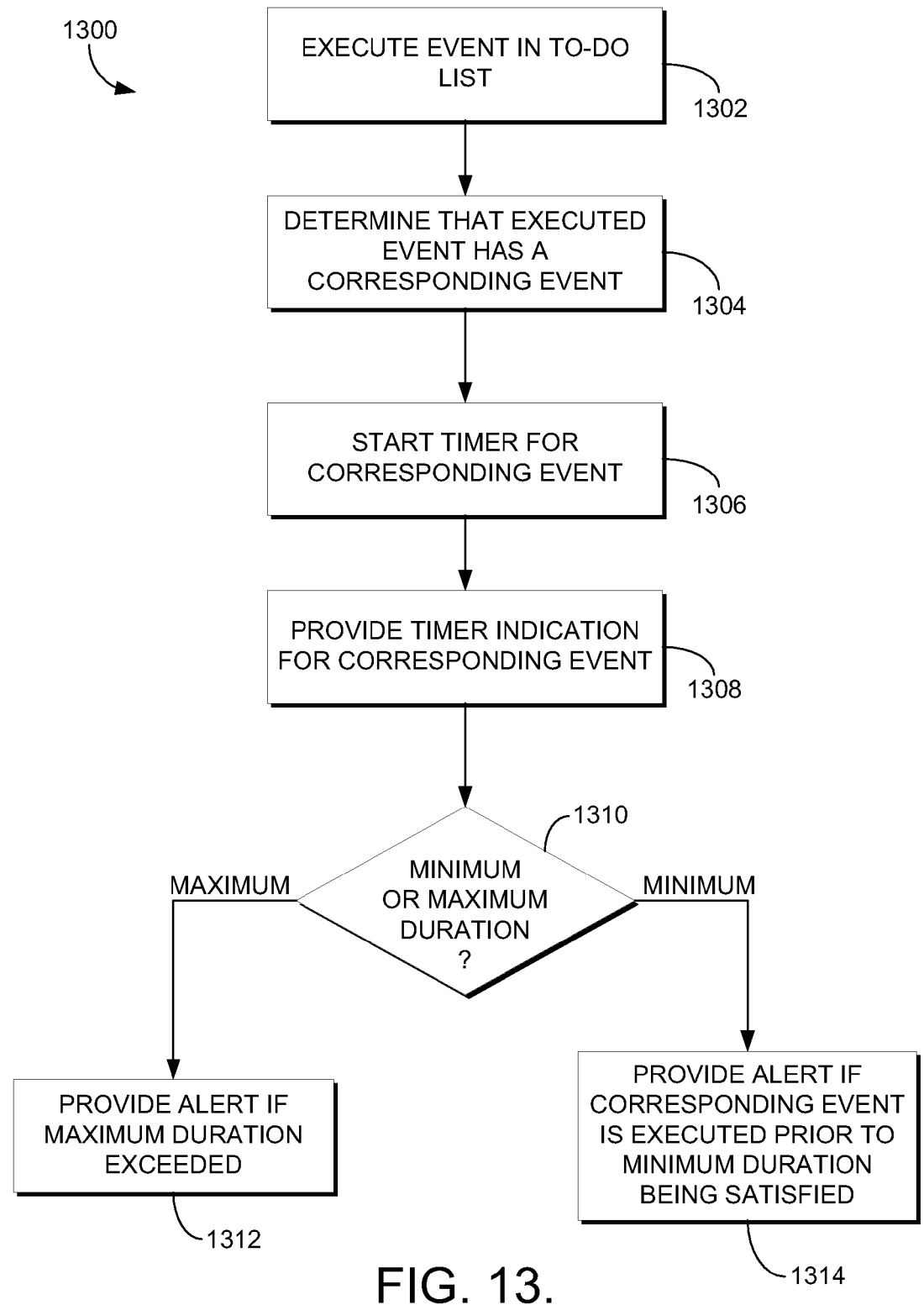
FIG. 13 is a flow diagram showing a method for providing timer and/or reminder functionality for an event in a to-do list corresponding with an event in the to-do list that has been executed in accordance with an embodiment of the present invention.

Referring now to FIG. 13, a flow diagram is provided illustrating a method 1300 for automatically providing timer and/or alert functionality for an event in a to-do list corresponding with an event that has been executed in accordance with an embodiment of the present invention. Initially, as shown at block 1302, an event in a to-do list is executed. In response to the event execution, it is determined that there is a corresponding event associated with the executed event, as shown at block 1304. A timer is started for the associated event, as shown at block 1306. Additionally, a timer indication is provided in association with the corresponding event in the to-do list, as shown at block 1308. A determination may be made, such as that shown at block 1310, whether the corresponding event has an associated maximum duration not to be exceeded or a minimum duration to be satisfied before execution of the event. If the corresponding event has an associated maximum duration, an alert is provided if the maximum duration is exceeded prior to the execution of the event, as shown at block 1312. Alternatively, if the corresponding event has an associated minimum duration, an alert is provided if a clinician attempts to execute the event before the minimum duration has been satisfied, as shown at block 1314.

As indicated previously, in some cases, multiple clinicians participating in the same clinical care process may each have a separate to-do list. In some embodiments, to-do events may be shared between two or more to-do lists. For example, when a macro is selected and executed, the macro may generate a to-do list for two or more clinicians. In some cases, one or more events may be performed by any one of those clinicians. Accordingly, the macro may automatically populate two or more to-do lists with shared events. When a shared event is executed by one of the clinicians via that clinician's to-do list, the event is shown as completed in all to-do lists in which the event was included.

As can be understood, embodiments of the present invention provide to-do lists within a computerized healthcare environment for tracking and documenting events. Embodiments of the present invention also provide timer and reminder functionality in conjunction with such to-do lists. Embodiments of the present invention further allow events to be shared among multiple to-do lists.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A method for providing an electronic to-do list for tracking completion of a plurality of clinical events during a clinical care process, the method comprising:

receiving a user selection of a to-do macro for a clinical care process for a patient, the to-do macro comprising data associated with a plurality of clinical events to be completed for the clinical care process for the patient;

presenting a to-do macro user interface in response to the user selection of the to-do macro, the to-do macro user interface including an indication of the plurality of clinical events;

receiving, through the to-do macro interface before the separate to-do list is generated, user input indicating which of the clinical events should be included in a to-do list when the to-do macro is executed;

receiving, through the to-do macro interface before the separate to-do list is generated, additional user input indication that one or more of the plurality of clinical events has already been completed for the patient;

receiving, through the to-do macro interface before the separate to-do list is generated, further user input modifying patient information associated with at least one of the clinical events;

generating, at a computing device, a separate to-do list customized for a clinician and the patient involved in the clinical care process based on the selected to-do macro and the user input, additional user input, and further user input received via the to-do macro user interface, the separate to-do list providing an indication of clinical events that are to be performed by the clinician on the patient and that the one or more clinical events has already been completed, wherein multiple clinicians are involved in the clinical care process and the multiple clinicians are individually assigned to complete different clinical events within the plurality of clinical events;

presenting, at a computing device, the separate to-do list to a user via a user interface;

receiving, at a computing device, user input indicative of completion of one or more selected clinical events on the patient that are indicated on the separate to-do list; and based on the user input, providing an indication that the one or more selected clinical events have been completed.

2. The method of claim 1, wherein the method further comprises defining the to-do macro by identifying the plurality of clinical events based on a pre-built standard of care for the clinical care process developed to ensure patient quality of care.

3. The method of claim 1, wherein the method further comprises receiving user input modifying one or more clinical events in the separate to-do list.

4. The method of claim 3, wherein the user input modifying one or more clinical events in the separate to-do list comprises at least one of reordering one or more clinical events in the separate to-do list and modifying information associated with one or more clinical events in the separate to-do list.

5. The method of claim 1, wherein providing an indication that the one or more selected clinical events have been completed comprises removing the one or more selected clinical events from the separate to-do list.

6. The method of claim 1, wherein the method further comprises documenting the completion of the one or more selected clinical events in an electronic record.

7. A method for documenting a clinical event performed during a clinical care process, the method comprising:

receiving a user selection of a to-do macro for a clinical care process, the to-do macro comprising data associated with a plurality of clinical events to be completed for the clinical care process;

presenting a to-do macro user interface in response to the user selection of the to-do macro, the to-do macro user interface including an indication of the plurality of clinical events;

receiving, through the to-do macro interface before the separate to-do list is generated, user input indicating which of the clinical events should be included in a to-do list when the to-do macro is executed;

receiving, through the to-do macro interface before the separate to-do list is generated, additional user input indication that one or more of the plurality of clinical events has already been completed for the patient;

receiving, through the to-do macro interface before the separate to-do list is generated, further user input modifying patient information associated with at least one of the clinical events;

presenting, at a computing device, an electronic to-do list customized for a clinician and the patient based on the user input, the additional user input, and the further user input, the to-do list including an indication of a plurality of clinical events to be performed on the patient during a clinical care process by an individual clinician, wherein at least one clinical event is presented with details regarding how the at least one clinical event should be performed, wherein individual clinical events, within the plurality of clinical events, are performed on the patient by different clinicians during the clinical care process;

receiving, at a computing device, user input indicating that the at least one clinical event has been completed on the patient; and based on the user input, documenting the completion of the at least one clinical event in an electronic record for the patient, wherein the details associated with the at least one clinical event are used to populate information in the electronic record, thereby generating a record indicating that the at least one clinical event has been performed on the patient and a record that includes the details describing how the at least one clinical event was performed on the patient.

8. The method of claim 7, wherein presenting an electronic to-do list comprises receiving a selection of a to-do macro, to-do macro comprising information for the plurality of clinical events to be performed during the clinical care process.

9. The method of claim 8, wherein the method further comprises defining the to-do macro by identifying the plurality of clinical events based on a pre-built standard of care for the clinical care process developed to ensure patient quality of care.

10. The method of claim 7, wherein the method further comprises receiving user input modifying one or more clinical events in the to-do list.

11. The method of claim 10, wherein the user input modifying one or more clinical events in the to-do list comprises at least one of reordering one or more clinical events in the to-do list and modifying information associated with one or more clinical events in the to-do list.

12. The method of claim 7, wherein the details associated with the at least one clinical event comprises a series of answers, and wherein the series of answers correspond with a series of questions in an electronic record and are used to populate information in the electronic record.

13. A method for providing an electronic to-do list for tracking completion of a plurality of clinical events during a clinical care process and documenting the completion of at least one of the clinical events in an electronic record, the method comprising:

receiving a user selection of a to-do macro for a clinical care process, the to-do macro comprising data associated with a plurality of clinical events to be completed for the clinical care process, wherein at least one clinical event is associated with details regarding the at least one clinical event;

presenting a to-do macro user interface in response to the user selection of the to-do macro, the to-do macro user interface including an indication of the plurality of clinical events;

receiving, through the to-do macro interface before the separate to-do list is generated, user input indicating which of the clinical events should be included in a to-do list when the to-do macro is executed;

receiving, through the to-do macro interface before the separate to-do list is generated, additional user input indication that one or more of the plurality of clinical events has already been completed for a patient;

generating, at a computing device, a separate to-do list customized for a clinician and the patient involved in the clinical care process based on the selected to-do macro and the user input and the additional user input, the separate to-do list providing an indication of clinical events that are to be performed by the clinician;

presenting, at a computing device, the separate to-do list to a user via a user interface;

receiving, at a computing device, new user input indicative of completion of the at least one clinical event having details associated therewith; and based on the new user input, providing an indication that the at least one clinical event has been completed for the patient and documenting the completion of the at least one clinical event in an electronic record for the patient, wherein the details associated with the at least one clinical event are used to populate information in the electronic record, and wherein the indication that the at least one clinical event has been completed is removing the indication corresponding to the at least one clinical event from the separate to-do list and moving the indication corresponding to the at least one clinical event to a completed tab showing clinical events completed by the clinician.

14. The method of claim 13, wherein the details associated with the at least on clinical event comprises a series of answers, and wherein the series of answers correspond with a series of questions in an electronic record and are used to populate information in the electronic record.

* * * * *